United States Patent [19]

Calva-Mercado et al.

[11] Patent Number: 5,405,754
[45] Date of Patent: Apr. 11, 1995

[54] **PROCESS FOR OBTAINING AN ANTIGENIC REAGENT USEFUL FOR THE INDIRECT DETERMINATION OF *SALMONELLA TYPHI***

[75] Inventors: Edmundo Calva-Mercado, Cuernavaca Mor.; Guillermo M. Ruiz Palacios, Ursula Xitla México; Antonio V. Rodriguez, Col. Miraval; Yolanda L. Vidal, Col. E. Zapata México, all of Mexico

[73] Assignee: Universidad Nacional Autonoma de Mexico, Mexico City, Mexico

[21] Appl. No.: 673,006

[22] Filed: Mar. 21, 1991

[30] Foreign Application Priority Data

May 10, 1990 [MX] Mexico ................................. 20650

[51] Int. Cl.[6] .................. C12M 1/00; C12M 1/38; C12M 1/20
[52] U.S. Cl. ..................................... 435/34; 435/244; 435/245; 435/252.1; 435/879
[58] Field of Search ............... 435/244, 245, 252.1, 435/879, 34

[56] References Cited

U.S. PATENT DOCUMENTS 3,982,999  9/1976  Kharasch ........................... 424/94.3
4,578,270  3/1986  Csizer et al. ........................ 424/92

OTHER PUBLICATIONS

Comparative analysis of the *Salmonella typhi* and *Escherichia coli* ompC genes, Jose Luis Puente et al., Gene, 83 (1989) 197–206.
The Significance of Iron in Infection, J. J. Bullen, Review of Infectious Diseases, Nov.–Dec. 1981, vol. 3, No. 6.
Iron and Infection, Eugene D. Weinberg, Microbiological Reviews, Mar. 1978, pp. 45–66.
Research Opportunities in Typhoid Fever: Epidemiology and Molecular Biology, Edmundo Calva et al., Bio Essays, Nov. 1988, vol. 9, No. 5.
Summary of an International Workshop on Typhoid Fever, R. Edelman et al., Reviews of Infectious Diseases, May–Jun. 1986, vol. 8, No. 3.
Diagnostic Value of the Widal Test in Areas Endemic for Typhoid Fever, Myron M. Levine et al., Am. J. Trop. Med. Hyg., 1978, 27(f), pp. 795–800.
Counter immunoelectrophoresis (CIEP) for serological diagnosis of typhoid fever, Indian J. Med. Res. 84, Oct. 1986, pp. 353–357.
Comparison of Counter Current Immunoelectrophoresis and Widal Tests in the Diagnosis of Typhoid Fever in Childhood, Indian J. Pathol. Microbiol. 29, 1986, 21–26.
Antibody response to the lipopolysaccharide and protein antigens of *Salmonella typhy* during typhoid infection, R. S. Tsang et al., Clin. Exp. Immunol., 1981, 46:508–514.
Improved serodiagnosis of *Salmonella enteric* fevers by an enzyme-linked immunosorbent assay, W. J. Beasley et al., J. Clinical Microbiol., 1981, 13:106–114.
Antibodies to porin antigens of *Salmonella typhi* induced during typhoid infection in humans., I. Calderon et al., Infect. Immun. 1986, 52:209–212.
Enzyme-linked immunosorbent assay for detection of *Salmonella typhi* protein antigen, H. Appassakij et al., J. Clin. Microbiol., 1987, 25:273–277.

(List continued on next page.)

*Primary Examiner*—Michael G. Wityshyn
*Assistant Examiner*—Jane Williams
*Attorney, Agent, or Firm*—Finnegan, Henderson, Farabow, Garrett & Dunner

[57] ABSTRACT

The invention described herein consists of a process for preparing an antigenic reagent useful for the indirect determination of *Salmonella typhi*, the organism that is the causal agent of typhoid fever (TF). The invention consists on the following steps: to grow *Salmonella typhi* in a culture medium, characterized by containing a free-iron chelator, which generates a specific *S. typhi* outer membrane protein (OMP) pattern, OMPs that are used as a selective antigen for the detection of specific serum antibodies, by an immunoassay technique (ELISA).

13 Claims, No Drawings

OTHER PUBLICATIONS

Detection of *Salmonella typhi* protein antigen in serum and urine: A value for diagnosis of typhoid fever in an endemic area, N. Banchuin et al., Asian Pacific J. Aller. Immunol. 1987, 5:155–159.

Seradiagnosis of typhoid fever by enzyme–linked immunosorbent assay determination of anti-*Salmonella typhi* lipopolysaccharide antibodies, S. Nardiello et al., J. Clin. Microbiol., 1984, 20:718–721.

Serological diagnosis of typhoid fever by enzyme–linked immunosorbent assay (ELISA), L. Srivastava et al., Ann. Trop. Pediatrics 1986, 6:191–194.

Indirect Immunoglobulin G. (IgG) and IgM enzyme–linked immunosorbent assays (ELISAs) and IgM capture ELISA for detection of antibodies to lipopolysaccharide in adult typhoid fever patients in Pakistan, J. Sippel et al., J. Clinical Microbiol. 1989, 27:1298–1302.

Immunoblot detection of class–specific humoral immune response to outer membrane proteins isolated from *Salmonella typhi* in humans with typhoid fever, V. Ortiz et al., J. Clinical Microbiol. 1989, 27:1640–5.

Outer Membrane Protein Antigens in an Enzyme–Linked Immunosorbent Assay for *Salmonella* Enteric Fever and Meningococcal Meningitis, J. E. Sippel et al., J. Clin. Microbiol. 1987, 7:372–378.

J. Clinical Microbiology Apr. (1978) pp. 372–378 v. 7 n. 4.

Schraitman J Bacteriology vol. 108, No. 1 pp. 553–563 (1971).

Barnes et al cell vol. 22 pp. 649–655 (1980).

PROCESS FOR OBTAINING AN ANTIGENIC REAGENT USEFUL FOR THE INDIRECT DETERMINATION OF SALMONELLA TYPHI

BACKGROUND OF THE INVENTION

TF (typhoid fever) in man is the clinical manifestation of a generalized or systemic infection by *Salmonella typhi*, a gram-negative bacterium which penetrates the organism through the gastrointestinal tract, usually by ingestion of water or food contaminated by human feces. *S. typhi* belongs to the serotype 9, 12, d, Vi, defined by the repeated sugar units (9, 12) of the O antigen, that together with lipid A constititutes the lipopolysaccharide (LPS) of the outer membrane; by the H antigen (d) constituted by the flagellar protein or flagellin, and by the Vi antigen or K capsular polysaccharide (Calva, E. et al., 1988, Research opportunities in typhoid fever: Epidemiology and Molecular Biology. *BioEssays* 9: 173-177).

As other gram-negative bacteria, *S. typhi* has three envelopes, constituted by two membranes, the internal and external, and an intermediate cell wall or peptidoglycan.

One of the major *S. typhi* outer membrane proteins (mOMPs) is OmpC (Puente J.L. et al., 1987, Isolation of an OmpC-like outer membrane protein gene from *Salmonella typhi*. *Gene* 61: 75-83.) The composition of the gene that codifies OmpC is very similar to that from *E. coli* (Puente, J.L. et al.) Comparative analysis of the *Salmonella typhi* and *Escherichia coli* OmpC genes. *Gene* 83: 197-206). OmpC (a porin) in *E. coli* forms a trimer that constitutes a 1.1 amstrong-diameter pore, which allows the passing of hydrophilic molecules. In *E. coli*, OmpF (a porin) forms trimers that constitute 1.2 amstrong-diameter pores. Another mOMP is OmpA which is a structural monomer.

In addition, in both: *E. coli* and in *S. typhimurium* exist a variety of proteins, some of which are regulated by metabolites such as calcium, phosphate, iron, maltose and others. To this respect, in the case of iron (Fe) it has been observed that there is a competition for this metal, between the host and the invader in such a way that both have developed different mechanisms for its acquisition or its sequestering during infection (Bullen, J.J., 1981, The significance of iron in infection. *Rev. Infect. Dis.* 3: 1127-1138; Weinberg, E.D., 1978, Iron and Infection. *Microbiol. Rev.* 42: 45-66).

It is evident that typhoid fever affects individuals from different geographical areas, ages and socioeconomical levels; thus there is in consequence a great need for new, highly sensitive and specific, rapid, and easy to perform diagnostic tests, for detecting TF in such a manner that it can be easily distinguished from other febrile diseases. This is even more important for children, in view that they tend to develop mild forms of the disease (Ferreccio, C. et al., 1984, Benign bacteremia caused by *S. typhi* and *S. paratyphi* in children younger than two years. *J. Pediatr.* 104: 899-901). Due to the fact that the majority of the population in areas where TF is endemic has high levels of serum antibodies against *S. typhi*, induced by its continuous exposure to the microorganism, the serological tests performed in these areas are of low specificity for the diagnosis of TF. Moreover, a significant increase in the antibody titers against the O antigen usually is detected until the second or third week after onset of fever. (Calva et. al. 1988 Research Opportunities in typhoid Fever: Epidemiology and Molecular Biology. Bioessays 9:173-177).

To date, the most exact diagnostic test for TF is the isolation of *S. typhi* from bone marrow aspirates, which has a 70 to 90% sensitivity and specificity. Nevertheless, it is an aggressive procedure and can only be performed in some hospitals, thus it is an impractical test. Blood cultures or hemocultures are more commonly used and easy to perform, although their sensitivity is also 70-90% when three consecutive cultures are done, at 1-2 day intervals. The important disadvantages related to this method are that the isolation and identification of *S. typhi* takes at least 72 hours and that the hemocultures might not be highly sensitive, due to a low concentration of circulating *S. typhi* in blood (approximately 20 cells/ml or less), especially when the patients have taken antibiotics before the culture, a common situation in many countries (Edelman, R. and Levine M.M., 1986, Summary of an international workshop on typhoid fever. *Rev. Infect. Dis.* 8: 329-350).

In some investigations performed with different antigenic reagents, of non-proteic nature, and with different methodologies, varied results have been observed. For instance, one of the most used serodiagnostic methods for TF, and one of the oldest, is the Widal test or "febrils reactions", that consists in the detection of agglutination in a suspect serum with the O and H antigens. With this test it is possible to diagnose enteric fever mainly by *S. typhi* and *S. paratyphi*. Nevertheless, due to the elevated background titers in healthy individuals in endemic areas, its use is recommended for individuals from non-endemic areas and to persons below ten years of age in endemic areas (Levine M.M. et al., 1978, Diagnostic value of the Widal test in areas endemic for typhoid fever. *Am. J. Trop. Med. Hyg.* 27: 795-800).

The counter immuno electrophoresis (CIE) method has also been used, utilizing various antigenic extracts. With an antigenic extract obtained by sonication, the best results were obtained, i.e. a sensitivity and specificity for TF of 70 and 96%, respectively (Talwar, V. et al, 1986, Counter ion immuno electrophoresis (CIEP) for serological diagnosis of typhoid fever. *Indian J. Med. Res.* 84: 353-357). By solid-phase radioimmuno assay (RIA), positive values were obtained among 94% and none of TF patients and healthy controls, respectively. In contrast, the same values for the Widal test were 81 and 25% (Tsang, R.S.W. et al., 1981, Antibody response to the *lipopolysoccharide* and protein *antigens* of *S. typhi* during typhoid infection. *Clin. Exp. Immunol.* 46: 508-514). Another group found that CIEP had a sensitivity of 90% for diagnosing TF in culture-negative clinically diagnosed TF patients, as compared with 48% obtained with the Widal test (Srivastava, V.K. et al., 1986, Comparison of counter current immunoelectrophoresis and Widal tests in the diagnosis of typhoid fever in childhood. *Indian J. Pathol. Microbiol.* 29: 21-26).

The ELISA (enzyme-linked immunosorbent assay) has been used by different groups interested in the diagnosis of TF, using practically all the surface antigens described, treated or obtained by variable ways, has led to the obtention of variable results.

Beasley, W.J. et al. (1981, Improved serodiagnosis of Salmonella enteric fevers by an enzyme-linked immunosorbent assay. *J. Clin. Microbiol.* 13: 106-114), performed an ELISA using a proteic antigen. In their work they developed tests with TF and paratyphoid (PTF) patients; they could detect as positives some samples that appeared to be false negatives by the Widal (agglutination) test. Nevertheless, the percent of positive values was indistinct for TF and for PTF and, on the other hand, there was great dispersion among the positive values; for this reason it was not possible to propose a cutoff line at one serum dilution. Also, when the immune response was evaluated by immunoglobulin G (IgG) and by immunoglobulin M (IgM), no significant difference was observed in the IgM and IgG titers between sera from acute and convalescent phase individuals. Lastly, sera from persons with other kinds of infections different from enteric fever were not evaluated.

Calderon, I. et al. (1986, Antibodies to porin antigens of *S. typhi* induced during typhoid fever in humans. *Infect. Immun.* 52: 209–212), titrated the immune response to *S. typhi* OMPs with IgG and IgM by ELISA, and found that the absorbance values obtained with porins, presumably free of lipopolysaccharide (LPS), with sera positive for TF, differed significantly from control sera of clinically healthy individuals from an endemic area. They also compared this response with that obtained against the LPS and flagellin, observing a greater response against the porins. Nevertheless, in their assay they did not evaluate subjects with other kinds of infections.

Appassakij, H. et al. (1987, Enzyme-linked immunosorbent assay for detection of *S. typhi* protein antigen. *J. Clin. Microbiol.* 25: 273–277), designed an ELISA method for the determination of proteic antigen in serum. When they tried it on groups of subjects with TF, PTF, other febrile diseases, as well as in healthy controls, they observed a great dispersion in the TF and PTF groups and a certain degree of crossing-over when a cutoff value was established. They obtained an 84% sensitivity and an 89% specificity.

The ELISA was tested by Banchuin, N. S. et al. (1987, Detection of *S. typhi* protein antigen in serum and urine: a value for diagnosis of typhoid fever in an endemic area. *Asian Pacific J. Allergy Immunol.* 5: 155–159), for detecting antigen in serum and in urine; and they compared it with the Widal test. With this assay they obtained a predictive positive value of 33% in serum and 64% in urine; against 17% in Widal-O and 13% in Widal-H. Their negative predictive value was 97% in serum and urine, and of 97% in the Widal reactions. With these results, they demonstrated that the assay was significantly superior to the Widal test in the positive predictive value, and that the Widal is of low value for adults in endemic areas, as previously pointed out by Levine, M.M. et al. (1978, Diagnostic value of the Widal test in areas endemic for typhoid fever. *Am. J. Trop. Med. Hyg.* 27: 795–800), and Lambertucci, J.R. et al. (1985, The value of the Widal test in the diagnosis of prolonged septicemic salmonellosis. *Rev. Inst. Med. Trop. Sao Paulo* 27: 82–85).

Use of the ELISA for detecting antibodies to *Salmonella typhi* lipopolysaccharide (LPS) has been reported. In two reports the LPS-ELISA was found to be more specific and more sensitive, respectively than the Widal test. In one study, the % of serum samples positive for LPS immunoglobulins ranged between 83 and 97% versus 0 to 4% in healthy controls; for the Widal test these values ranged between 41 and 90%, and 0 and 4%, respectively, although they were obtained at lower dilution of the test serum. Nevertheless, there was wide scattering of the data, making it difficult to set a cutoff value between positive and negative values. In addition, lower dilutions of the test serum, than the ones reported below in the FT-ELISA described in this invention, were used for the LSP-ELISA (Nardiello, S. et al., 1984, Serodiagnosis of typhoid fever by enzyme-linked immunosorbent assay determination of anti-*Salmonella typhi* lipopolysaccharide antibodies. *J. Clin. Microbiol.* 20: 718–721). In another report, even lower dilutions of the test serum were used, wide scattering of the data was obtained, and positive values for only 73 to 82% of the bacteriologically proven cases were obtained. Nevertheless, positive values with the Widal test were present in only 41% of the samples (Srivastava, L. and Srivastava, V.K., 1986, Serological diagnosis of typhoid fever by enzyme-linked immunosorbent assay [ELISA]. *Annals of Tropical Paediatrics* 6: 191–194).

After analyzing the above mentioned data with respect to the protein-ELISAs, one can conclude that, in spite of the various investigations in this field, performed mainly in areas where TF is endemic, and of the important efforts that have been made for diagnosing efficiently this disease, there is still no diagnostic system for TF that is rapid, sensitive, specific, reproducible, practical, and economical. Thus, a process has been developed for obtaining and utilizing an antigenic reagent that, due to its characteristics, allows the indirect determination of *Salmonella typhi*, the casual agent of TF.

SUMMARY OR THE INVENTION

The invention presented here refers to a process for obtaining an antigenic reagent useful for determining indirectly *Salmonella typhi*. Growth of the bacteria is done in a culture medium, with an added free-iron chelating agent, up to late logarithmic phase of growth. Afterwards, the culture is centrifuged, and the resulting pellet is resuspended in a buffer solution; this solution is subjected to sonication in ice with seven pulses of 30 sec each; the sonicated suspension is centrifuged, the resulting supernatant is collected and centrifuged at 3° to 10° C., the resulting pellet is resuspended in a buffer solution, with triton X-100 at 1 to 4%; the suspension is incubated for 10 to 25 min at 20° to 41° C., it is centrifuged at 3° to 10° C., and the resulting pellet is resuspended in a buffer solution.

The above suspension is centrifuged for 20 to 40 min at a temperature of 3° to 10° C. The resulting pellet is resuspended in 400 microliters of a buffering solution, with a pH of 7.0 to 7.8, which is made 0.5 to 2.0% in 2-mercaptoethanol, and 0.5 to 2.0% in sodium dodecyl sulphate (SDS). Thus the desired antigen is obtained (outer membrane protein preparation).

The free-iron chelating agent in the culture medium has the purpose of providing one condition similar to that found in the bloodstream; this results in a characteristic OMP electrophoretic pattern which has a selective influence on the antibodies detected by the ELISA.

An objective of the present invention is to provide the methodology for obtaining a proteic reagent for the indirect determination of *Salmonella typhi* by ELISA, which presents some advantages, such as: rapid detection, since the maximum time for observing a result is five-and-a-half hours; small sample size (less than 0.1 ml), which is obtained by a single venous puncture; and that no serial sampling has to be done.

Another of the objectives of the invention is to provide the methodology for the treatment of the OMP preparation such that protein denaturation is favored, previous to the sensitization of the ELISA microplate, so that there is a selective effect over the variance increment between the immunoresponse from positive and negative subjects to TF.

One more objective of the invention is to provide an antigen with which defined results can be obtained, since it is possible to propose a cutoff value at a defined serum dilution where the positive sera present slight dispersion, that is: a geometric mean of 1.41, with a standard deviation of 0.122 and maximum and minimum values of 1.58 and 1.22, respectively. This geometric mean was 2.47 to 2.76-fold greater (2.6 on the average) than the mean values in the control groups. The sensitivity and specificity is 100%.

DETAILED DESCRIPTION OF THE INVENTION

Upon describing in detail the process for preparing an antigenic reagent useful for detecting *Salmonella typhi* indirectly, the object of this invention, the observation is made that this description illustrates the form and manner of making such preparation, but that this process can undergo modifications in detail without varying fundamentally and thus without altering the essence of the procedure. In practice, if the circumstances warrant a modification, these will be performed without losing the true objective of the invention. The results obtained by the applying party, for diagnosing efficiently TF, validate the OMP-ELISA as rapid, sensitive, specific, practical, and economic, through treatment of the antigen by the procedure subject of the invention.

*Salmonella typhi* Ty2 (serotype 9, 12, d, Vi), American Type Culture Collection No. 19430, was used as reference strain.

Two basic culture media were used for growing *Salmonella typhi*. One was medium "A" (nutrient) and the other was medium "T" (minimal medium); containing the following ingredients:

| MEDIUM "A" | |
|---|---|
| Nutrient broth (Difco) | 7 g |
| Yeast extract (Difco) | 1 g |
| Glycerol | 2 ml |
| $K_2HPO_4$ | 3.7 g |
| $KH_2PO_4$ | 1.3 g |
| $H_2O$ | up to one liter |
| MEDIUM "T" | |
| NaCl | 5.8 g |
| KCl | 3.7 g |
| $CaCl_2.2H_2O$ | 0.15 g |
| $MgCl_2.7H_2O$ | 0.10 g |
| $NH_4Cl$ | 1.1 g |
| $FeCl_3$ | $2.7 \times 10^{-4}$ g |
| $Na_2PO_4$ | 0.142 g |
| $KH_2PO_4$ | 0.272 g |
| 50% glucose | 10 ml |
| Tris-HCl | 12.1 g |
| $H_2O$ | up to one liter |

The pH is adjusted to 7.4 with concentrated HCl
The phosphate-buffered saline (PBS) contains:

| NaCl | 16 g |
|---|---|
| $Na_2HPO_4$ | 5.8 g |
| $KH_2PO_4$ | 6.4 g |
| KCl | 0.4 g |
| double-distilled $H_2O$ | up to two liters |

The pH is adjusted to 7.4 or 7.8 with concentrated HCl

The antigen, subject of this invention, was obtained using methods based on those described by Schnaitman C.A. (1971, Effect of ethylene diamine tetracetic acid, triton X-100, and lysozyme on the morphology and chemical composition of isolated cell walls of *Escherichia coli. J. Bacteriol.* 108: 553-556) or METHOD I; and by Matsuyama, S.I. et al. (1984, Promoter exchange between ompF and ompC genes for osmoregulated major outer membrane protein genes of *Escherichia coli* K-12. *J. Bacteriol.* 158: 1041-1047) or METHOD II.

The above published methods are for obtaining outer membrane protein preparations from *Escherichia coli*; having modified them for use on *Salmonella typhi* is not known as described herein.

The new technique includes the use of some additional compounds, thus some unexpected results have been produced. These additional compounds are:
sucrose
human transferrin
conalbumin or egg-white transferrin
2,2' dipyridyl, and
$FeCl_3$ Sucrose is used for rendering a change in osmolarity in the culture medium, 10% being equivalent to 300 mM NaCl, i.e. corresponding to the osmolarity found in human serum. The transferrins and 2,2', dipyridyl were used for chelating and thus diminishing the levels of free iron; $FeCl_3$ was for increasing the level of iron in the culture medium.

METHOD I a) Cells were grown in 50 ml of culture medium "A", incubating at a temperature between 20° and 41° C., up to late logarithmic phase of growth.

b) A cell pellet is obtained by centrifugation for 5 min at 20 krpm, utilyzing a Beckman A-20 rotor.

c) The pellet is resuspended in 15 to 30 ml of N-2 hydroxy ethyl piperazine N'-2-ethanesulfonic acid (HEPES), pH 6.5 to 8.0; preferably from 7.0 to 7.8.

d) The suspension is centrifuged for 10 to 20 min at 6 krpm.

e) The pellet is resuspended in 15 to 30 ml of a buffer solution. HEPES 10-15 mM, at pH 7.0 to 7.8.

f) The suspension is centrifuged for 10 to 20 min at 6 krpm.

g) The pellet is resuspended in 15 to 30 ml of HEPES 10-15 mM, at pH 7.0 to 7.8.

h) The suspension is sonicated in ice with seven pulses (180 watts), of 30 sec each, with intervals of the same duration, in an MSE Soniprep 150 sonicator.

In between the 4th and 5th pulses, when the O.D.660 of the suspension is around 0.6-0.7, the following compounds are added:
50 microliters of 1M $MgCl_2$
2 microliters of 10 mg/ml DNase
5 microliters of 10 mg/ml DNase i) The sonicated suspension is centrifuged twice for 15 to 25 min at 5 krpm; collecting each time the supernatant.

j) The supernatant is centrifuged for 30 min at 50 krpm at a temperature of 3° to 10° C., utilyzing a Beckman 55.1 Ti rotor.

k) The pellet is resuspended in 15 to 30 ml of 10 mM HEPES, pH 7.0 to 7.8.

l) The suspension is centrifuged for 30 to 50 min at 45 krpm at a temperature of 3° to 10° C.

m) The pellet is resuspended in 5 to 20 ml of HEPES, pH 7.0 to 7.8.

n) The supension is centrifuged at 45 krpm for 30 to 50 min, at a temperature of 3° to 10° C.

o) The pellet is resuspended in 5 to 20 ml of 10 mM HEPES, 1 to 4% triton X-100.
p) The suspension is centrifuged for 30 to 50 min at 45 krpm at a temperature of 3° to 10° C.
q) The pellet is resuspended in 10 ml of 5 mM EDTA (ethylene diamine tetracetic acid), 50 mM Tris-HCl pH 7.8, triton x-100 1 to 4%.
r) The suspension is incubated for 10 to 25 min at a temperature of 20° to 41° C.
s) The suspension is centrifuged for 30 to 50 min at 45 krpm at a temperature of 20° to 41° C.
t) The pellet is resuspended in 0.5 to 2 ml of 10 mM HEPES, pH 7.0 to 7.8; thus the desired antigen is obtained.

METHOD II a) The cells were grown in 50 ml of culture medium "A" incubating at a temperature of 20° to 41° C., up to late logarithmic phase of growth.
b) The culture is centrifuged for 5 to 20 min at 10 krpm, using a Beckman JA-20 rotor.
c) The pellet is resuspended in 15 to 30 ml of 10–15 mM phosphate ($Na_2HPO_4$) buffer, pH 6.5 to 8.0; preferably between 7.0 and 7.5.
d) The suspension is centrifuged for 5 to 20 min at 10 krpm at a temperature of 3° to 10° C.
e) The pellet is resuspended in 15 to 30 ml of a 10–15 mM phosphate buffer, pH 7.0 to 7.5.
f) The suspension is sonicated over ice with seven pulses of 30 sec each, with 30 sec intervals, in an MSE Soniprep 150 sonicator.
g) The sonicated suspension is centrifuged for 5 to 20 min at 3 krpm at a temperature of 3° to 10° C., and the supernatant is collected.
h) The supernatant is centrifuged for 20 to 40 min at 40 krpm at a temperature of 3° to 10° C.
i) The pellet is resuspended in 15 to 30 ml of a 10–15 mM phosphate buffer, pH 7.0 to 7.5, 1–4% triton X-100.
j) The suspension is incubated for 10 to 25 min at a temperature of 20° to 41° C.
k) The suspension is centrifuged for 20 to 40 min at 40 krpm at a temperature of 3° to 10° C., in A Beckman 55.1 Ti rotor.
l) The pellet is resuspended in 15 to 30 ml of 10 mM phosphate buffer, pH 7.0 to 7.5.
m) The suspension is centrifuged for 20 to 40 min at 40 krpm at a temperature of 3° to 10° C.
n) The pellet is resuspended in 400 microliters of PBS, pH 7.0 to 7.5, containing 0.5 to 2.0% 2-mercaptoethanol and 0.5 to 2.0% SDS, thus the desired antigen is obtained.

When the OMP preparations (the above mentioned desired antigen) were analyzed by SDS-polyacrylamide gel electrophoresis, three main bands were observed, which correspond to the following proteins: OmpC of 38.5 kDa apparent molecular weight (Puente et al., 1987, op. cit.), OmpF of 37.5 kDa, and OmpA 31.5 kDa.

VARIATIONS IN GROWTH CONDITIONS

Osmolarity

With the purpose of identifying which bands corresponded to the OmpC and OmpF proteins, we analyzed the outer membrane proteins from cultures grown in high and low osmolarity. Thus, the bacteria grew in nutrient broth with 20% sucrose, which increases the culture osmolarity; a lower expression of a 37.5 kDa band was observed, which was denominated OmpF, on the basis of what has been reported for *E. coli* (Nakae, 1986).

When growth was performed in 10% sucrose, equivalent to the osmolarity of 0.87% NaCl found in human serum, the same efect for OmpF was found, although to a lesser extent.

Temperature

The cultures were normally incubated at 20° C. In nutrient broth incubated between 20° and 41° C., the late logarithmic phase was reached after seven hours, while at 20° C. it took 15 hours, having started with the same size inoculum. The cellular mass obtained at 20° C. represented 82.6% relative to that obtained at 41° C., as measured by absorbance at a wavelength of 660 nm.

Level of Free Iron

In order to analyze the effect of the levels of free iron (Fe) in OMP expression, two conditions were evaluated: limiting free iron against excess free iron, excess being considered the quantity present in the culture media utilized. In order to limit the access of this metal to the bacteria in the culture medium, different strategies were used.

a) No addition of iron to medium "T" or to minimal medium.
b) Trapping of traces of this metal with an inorganic chelator, 2,2' dipyridyl.
c) Utilization of two organic chelators, human transferrin and hen egg transferrin or conalbumin.

Bacterial growth in "T" medium with no added iron did not present important differences when compared with medium with added iron; if any, there was a greater expression of OmpA with respect to OmpC and OmpF.

With respect to the addition of chelators, utilization of 2,2' dipyridyl at concentrations of 100 μm and 150 μm in both culture media used, resulted in the overexpression or expression of several proteins with the following approximate molecular weigths: 48, 72, 77, 82, 92, 97 and 103 kDa.

The straining intensity of some bands corresponding to these proteins was a reflection of their higher level of expression, thus the 77 and 82 kDa proteins were considered as principal, and the rest as secondary. A band that appears to be present only in low free iron conditions was one of 48 kDa; although the 72 and 82 kDa protein bands were at a very low level in excess free iron.

With respect to the relationship chelator-culture medium, utilization of transferrin in "T" medium appears not to have a different effect on the above mentioned proteins than 2,2' dipyridyl; also, 2,2' dipyridyl produces a lower effect in nutrient medium with respect to that observed, at the same concentration, in minimal medium (Table 1).

The immune response was evaluated using OMPs from *S. typhi* grown in the selected media, with the following characteristics:

a) Low osmolarity
b) High osmolarity (10% sucrose)
c) Excess free iron
d) Limited free iron by:
   2,2' dipyridyl
   human tranferrin
   conalbumin The obtained results are shown in Table 1.

TABLE 1

GROWTH OF *Salmonella typhi* IN DIFFERENT FREE-IRON CONDITIONS.

| Culture medium | FeCl$_3$ | | | 2,2'Dip * | Trans ** | Sac *** |
|---|---|---|---|---|---|---|
| Times (hrs) | 1 μM | 10 μM | 100 μM | | | |
| | required for reaching late exponential phase | | | | | |
| "A" medium | 7.5 | 7.5 | 6 | 7 | 8 | 6 |
| "B" medium | 11 | 11 | 10 | 10 | 23 | 23 |

\* 2,2'- dipyridyl: growth was apparently the same at 100 or 150 μM.
\*\* Transferrin: Concentration was 2.5 mg/ml. Growth was apparently the same using either human transferrin or conalbumin.
\*\*\* Sucrose: growth was apparently the same in either 10 or 20% sucrose.

The initial inoculum was 100 μl of a 16 hour overnight culture per 50 ml of culture medium.

The immune response associated to the antigen obtained from bacteria grown in different conditions presented a greater variance with antigen from high osmolarity cultures, when compared to that obtained from low osmolarity conditions. In the same manner, a greater variance was observed with antigen synthesized under free iron limitation than under excess free iron. Nevertheless, in both cases the differences were not statistically significant.

The antigen was resuspended in either of the following three different solutions, previous to its immobilization in the ELISA microplates:

a) 10 mM Na$_2$HPO$_4$, pH 7.0 to 7.8.
b) Alkaline phosphate buffer (PBS), pH 7.0 to 7.8.
c) Alkaline phosphate buffer (PBS), pH 7.0 to 7.8, plus 0.5 to 2.0% sodium dodecyl sulphate (SDS), and 0.5 to 2.0% 2-mercaptoethanol (B-1).

The results obtained by these treatments revealed that there was no difference between using Na$_2$HPO$_4$ or PBS alone. In contrast, it was observed that the variance between positive and negative subjects for TF increased when B-1 was used. Furthermore, when the OMP preparations were boiled during 3 to 8 min in B-1, the variance increased further. The results obtained with sera from patients positive for TF show a standard deviation of 0.122 with an arithmetic mean of 1.41. B-1 probably has a denaturing effect over the proteins. The concentration of antigen in the ELISA microplates was 5 μg per ml.

In order to evaluate the optimum serum dilution in the immune response, by variance analysis, inverse dilutions of 125, 625, 3 125, and 15 625 were evaluated, comparing sera of subjects positive to TF against sera of two groups of subjects negative to TF. The latter were adults infected with enterotoxigenic *Escherichia coli*, and 1-2 year old children infected by *Campylobacter jejuni*. The reciprocal dilution that presented the greatest variance was 3 125. The enzyme-substrate reaction time was evaluated by a variance analysis at 5, 10, 20 and 30 min; 20 min was the selected time.

In summary, the following conditions were selected for the ELISA:

| | |
|---|---|
| antigen concentration (OMP preparations) | 5 μg/ml |
| serum dilution | reciprocal of 3 125 |
| conjugate dilution | reciprocal of 1 000 |
| enzyme-substrate reaction time | 20 min |
| resuspension of the antigen in alkaline phosphate buffer (PBS), pH 7.0 to 7.8, plus 0.5 to 2.0% sodium dodecyl sulphate (SDS), and 0.5 to 2.0% 2-mercaptoethanol (B-1); and boiled for 3 to 8 min. | |
| absorbancy (wave length) | 492 nm. |

The utilized sera were classified in the following manner: GROUP 1: TYPHOID FEVER; sera from 15 adults, symptomatic for typhoid fever and with a positive *Salmonella typhi* hemoculture, all during the first week of disease.

Controls

GROUP 2: sera from 15 adults, with diarrhea and positive stool cultures for enterotoxigenic *Escherichia coli*. GROUP 3: sera from 15 children, 1 to 2 years old, from a semi-urban cohort study, with positive stool cultures for *Campylobacter jejuni*. GROUP 4: sera from 15 clinically healthy adults. GROUP 5: sera from 15 adults bacteremic for: *Proteus* spp., *Salmonella enteritidis*, *Salmonella* spp., *Salmonella* group "B", *Candida albicans*, *Escherichia coli*.

The results obtained are presented in Table 2.

TABLE 2

ELISA-OMP IN PATIENTS WITH TF AND OTHER INFECTIONS

| Group | Average | Standard Deviation | Standard Error | Minimum | Maximum |
|---|---|---|---|---|---|
| 1 | 1.41 | 0.122 | 0.032 | 1.22 | 1.58 |
| 2 | 0.57 | 0.084 | 0.022 | 0.46 | 0.73 |
| 3 | 0.55 | 0.162 | 0.042 | 0.33 | 0.86 |
| 4 | 0.51 | 0.089 | 0.023 | 0.32 | 0.65 |
| 5 | 0.53 | 0.260 | 0.070 | 0.22 | 1.02 |

Groups 1 to 5 are as described previously.

The results obtained from the five groups were subjected to a variance analysis, and the probability of TF in group 1 versus groups 2, 3, and 4, was 0.001.

The absorbance values were read at a wavelength of 492 nm.

From the above results, a statistically significant difference can be observed between the absorbance values obtained with sera from individuals positive for TF and the values obtained from sera of individuals negative for TF. This indicates a highly specific humoral response to the antigen during TF.

Therefore, the antigen obtained by the procedure described herein can be employed for selectively detecting antibodies by ELISA for the diagnosis of TF in an endemic area.

In the following examples different procedures for preparing the antigenic reagent of this invention, used for determining *Salmonella typhi*, are described. The various modes of preparation do not alter in essence the properties of the product antigen.

EXAMPLE 1

50 ml of culture medium "A" are made 1 μM in FeCl$_3$. This medium is inoculated with 0.1 ml of an *S. typhi* overnight culture, and is incubated at a temperature of 20° to 41° C., until the culture reaches late logarithmic phase of growth. The culture is centrifuged for 5 to 20 min at 10 krpm, utilizing the Beckman rotor JA-20; the pellet is resuspended in 15 to 30 ml of 10 mM Na$_2$HPO$_4$ pH 7.0 to 7.5; and the suspension is centrifuged 5 to 20 min at 10 krpm at a temperature of 3° to 10° C. The pellet is resuspended in 15 to 30 ml of 10 mM Na$_2$HPO$_4$ pH 7.0 to 7.5; the suspension is sonicated over ice with seven pulses of 30 sec each, at 30 sec intervals. The sonicate is centrifuged for 5 to 15 min at 3 krpm at a temperature of 3° to 10° C.; the supernatant is collected and centrifuged for 20 to 40 min at 40 krpm at a temperature of 3° to 10° C. The resulting pellet is resuspended in 15 to 30 ml of 10 mM Na$_2$HPO$_4$ pH 7.0 to 7.5, containing triton X-100 at 1-4%, and incubated for 10 to 25 min at a temperature of 20° to 41° C., and centrifuged for 20 to 40 min at 40 krpm at a temperature of 3° to 10° C. The pellet is resuspended in 15 to 30 ml of 10 mM Na$_2$HPO$_4$ pH 7.0 to 7.5; the suspension is centrifuged during 20 to 40 min at 40 krpm at a temperature of 3° to 10° C. The pellet is resuspended in 400 μl of alkaline PBS, pH 7.0 to 7.5 containing 0.2 to 2% 2-mercaptoethanol and 1% SDS. Thus the desired antigen is obtained.

EXAMPLE 2

The same procedure as for EXAMPLE 1 was followed, except that medium "A" was made 10 μM in FeCl$_3$.

EXAMPLES 3 AND 4

The same procedure as for EXAMPLE 1 was followed, but culture medium "A" was made 100 μM in 2,2 ' dipyridyl, instead of adding FeCl$_3$. The procedure is repeated adding 2,2' dipyridyl up to 150 μM.

EXAMPLES 5 AND 6

The same conditions for the procedure in EXAMPLE 1 were followed, with the exception that 2.5 mg/ml of human transferrin instead of FeCl$_3$ is added to culture medium "A". Alternatively, the procedure is repeated adding 2.5 mg/ml conalbumin or egg white transferrin. With the procedures for EXAMPLES 5 and 6 an antigen with 10% more efficacy was obtained than that from procedures in EXAMPLES 1 through 4.

EXAMPLES 7 AND 8

The same conditions were followed as for EXAMPLE 1, but 10% sucrose if added to culture medium "A" instead of FeCl$_3$. This provides a substantial change in medium osmolarity. The procedure is similarly repeated, except that the medium is made 20% in sucrose.

EXAMPLES 9 TO 11

The same procedure as for EXAMPLE 1 is followed, except that S. typhi is grown in culture medium "T", adding every time that the procedure is done either 1 μM, 10 μM, or 100 μM FeCl$_3$.

EXAMPLES 12 TO 17

The same procedure as for EXAMPLE 1 is followed, except that culture medium "T" is used; and to which either of the compounds signaled in EXAMPLES 3 to 8 are added.

EXAMPLE 18

The OMPs obtained in examples 1 through 17 are resuspended in alkaline PBS, pH 7.0 to 7.8; SDS is added to a final concentration of 0.5 to 2.0%, and 2-mercaptoethanol to 0.5 to 2.0%. The suspension is boiled for 5 min, thus obtaining the desired antigen.

EXAMPLE 19

Fifty ml of culture medium "A" are made 1 μM in FeCl$_3$, are inoculated with 0.1 ml of an overnight culture of S. typhi, are incubated at a temperature of 20° to 41° C. up to late logarithmic phase of growth, and are centrifuged for 5 to 20 min at 6 krpm, using rotor Beckman JA-20. The resulting pellet is resuspended in in 15 to 30 ml of 10 mM N-(2-hidroxyethyl) piperazine-N-(2-ethanesulfonic acid) (HEPES), pH 7.0 to 7.8 and centrifuged for 10 to 20 min at 6 krpm at a temperature of 3° to 10° C. The resulting pellet is resuspended in 15 to 30 ml of 10 mM HEPES, pH 7.0 to 7.8, and centrifuged for 10 to 20 min at 6 krpm. The resulting pellet is resuspended in 15 to 30 ml of 10 mM HEPES, pH 7.0 to 7.8. It is sonicated over ice with seven pulses (180 watts) of 30 sec each, at 30 sec intervals, in an MSE Soniprep 150 sonicator. Between the fourth and fifth pulse, when the OD at 660 nm is approximately 0.6 to 0.7, the following compounds are added: 50 μl of 1M MgCl$_2$, 2 μl of 10 μg/ml DNase, and 5 μl of 10 μg/ml RNase. The sonicated suspension is centrifuged twice for 15 to 25 min at 5 krpm, collecting each time the supernatant.

The resulting supernatant is centrifuged for 30 to 50 min at 45 krpm at a temperature of 3° to 10° C., in a Beckman 55.1 Ti rotor. The pellet is resuspended in 15 to 30 ml of 10 mM HEPES, pH 7.0 to 7.8, and centrifuged for 30 to 50 min at 45 krpm at 3° to 10° C. The pellet is resuspended in 5 to 20 ml of 10 mM HEPES, pH 7.0 to 7.8, and centrifuged for 30 to 50 min at 45 krpm at a temperature of 3° to 10° C. The resulting pellet is resuspended in 5 to 20 ml of 10 mM HEPES, with triton X-100 at 1–4%. The suspension is centrifuged for 30 to 50 min at 45 krpm at 3° to 10° C. The pellet is resuspended in 5 mM ethylene diamino tetra acetic acid (EDTA), 50 mM Tris-HCl (pH 7.0 to 7.8), triton X-100 at 1 to 4%, and incubated for 10 to 25 min at 20° to 41° C. The suspension is centrifuged for 30 to 50 min at 45 krpm at 20° to 41° C. and the resulting pellet is resuspended in 0.5 to 2.0 ml of 10 mM HEPES, pH 7.0 to 7.8, thus obtaining the desired antigen.

EXAMPLE 20

The same procedure as for EXAMPLE 19, except that culture medium "A" is made 10 μM in FeCl$_3$.

EXAMPLES 21 AND 22

The same procedure as for EXAMPLE 19, except that instead of adding FeCl$_3$ to culture medium "A", 2,2' dipyridyl is added at 100 μM. The procedure is repeated adding 2,2' dipyridyl at 150 μM.

EXAMPLES 23 AND 24

The same procedure as for EXAMPLE 19, except that instead of adding FeCl$_3$ to culture medium "A", 2.5 mg/ml of human transferrin are added. The procedure is repeated adding 2.5 mg/ml of conalbumin or egg white transferrin.

EXAMPLES 25 AND 26

The same procedure as for EXAMPLE 19, except that instead of adding FeCl$_3$ to culture medium "A", sucrose to 10% is added in order to provide a change in culture osmolarity. The procedure is repeated adding sucrose to 20%.

EXAMPLES 27 TO 29

The same procedure as for EXAMPLE 19, except that the culture is done in medium "T", and the procedure is repeated twice, adding once 10 μM FeCl$_3$, and 100 μM FeCl$_3$ the second time.

EXAMPLES 30 TO 35

The same procedure as for EXAMPLE 19, except that culture medium "T" is used, to which compounds pointed out in EXAMPLES 21 to 26 are added, respectively.

It must be understood that the examples described above in detail can suffer some changes and modifications, without losing the essence of the invention or the perspective of the annexed claims.

I claim:

1. A process for obtaining an antigen useful in an enzyme-linked immunosorbed assay (ELISA) for indirectly determining the presence of antibodies to *Salmonella typhi* in human sera, said process comprising the steps of:
   a) growing *Salmonella typhi* cells in a culture medium in the presence of a free-iron chelator, to induce the expression of four to seven *Salmonella typhi* outer membrane proteins, and incubating said *Salmonella typhi* cells at 20° C. to 41° C., up to late logarithmic phase of growth;
   b) centrifuging the culture during 5 to 20 minutes at 10,000 to 20,000 rpm;
   c) resuspending the resulting pellet in 15 to 30 ml of a 10 mM to 15 mM buffer solution, pH 6 to 8.0;
   d) centrifuging the resulting pellet for 5 to 30 minutes at 10,000 to 20,000 rpm at 3° C. to 10° C.;
   e) resuspending the pellet in 15 to 30 ml of a 10 to 15 mM buffer solution, pH 6.5 to 8.0;
   f) sonicating the suspension over ice with seven pulses of 30 seconds each, at 30-second intervals;
   g) centrifuging the sonicated suspension for 5 to 20 minutes at 3,000 rpm at a temperature of 3° C. to 10° C.;
   h) centrifuging the resulting supernatant for 20 to 40 minutes at 30,000 to 45,000 rpm at a temperature of 3° C. to 10° C.;
   i) resuspending the pellet in 15 to 30 ml of a 10 to 15 mM buffer solution, pH 6.5 to 8.0, wherein said buffer solution comprises nonionic detergent at 1% to 4%;
   j) incubating the resulting suspension for 10 to 25 minutes at a temperature of 20° C. to 41° C.;
   k) centrifuging the suspension at 30,000 to 45,000 rpm;
   l) resuspending the pellet in 15 to 30 ml of a 10 to 15 mM buffer solution, pH 6.5 to 8.0;
   m) centrifuging the suspension for 20 to 40 minutes at 30,000 to 45,000 rpm at 3° C. to 10° C.;
   n) resuspending the pellet in 400 $\mu$l of alkaline phosphate buffer saline, pH 6.5 to 8.0, wherein said buffer contains protein-denaturing agents, thus obtaining the antigen; and
   o) submitting said resuspension from step n) to thermal treatment.

2. The process of claim 1, wherein in step (f), between the fourth and fifth pulse, the following reagents are added in order to obtain a purer antigen: 20 $\mu$l to 50 $\mu$l of 1M MgCl$_2$, 1 $\mu$l to 4 $\mu$l of 10 mg/ml DNase, and 3 $\mu$l to 7 $\mu$l of 10 mg/ml RNase.

3. The process of claim 1, wherein said free iron chelator is selected from the group consisting of 2,2' dipyridyl, human transferrin and conalbumin.

4. The process of claim 3, wherein said 2,2' dipyridyl is added at 100 to 150 $\mu$M.

5. The process of claim 3, wherein said human transferrin or conalbumin is added in the amount of 1 to 5 mg/ml.

6. The process of claim 1, wherein said antigen obtained in step (n) is immobilized on the ELISA microplates.

7. The process of claim 1, wherein the buffer solutions of steps (c), (e), (i), (l), and (n) have a pH of 7.0 to 7.5, and comprise Na$_2$HPO$_4$ or N-(2-hydroxyethyl)-piperazine-N-(2-ethanesulfonic acid) (HEPES).

8. A process for obtaining an antigen useful in an ELISA assay for indirectly determining the presence of antibodies to *Salmonella typhi* in human sera, said process comprising the steps of:
   (a) growing *Salmonella typhi* in a culture medium in the presence of a free iron chelator to induce the expression of 4 to 7 *Salmonella typhi* outer membrane proteins; and
   (b) extracting said antigen from said *Salmonella typhi* cells.

9. The process of claim 1 wherein said thermal treatment comprises incubating the obtained antigen in a boiling water bath for 3 to 10 minutes.

10. The process of claim 1 wherein said denaturing agents are 2-mercaptoethanol and sodium dodecyl sulfate.

11. The process of claim 1, wherein said centrifuging of step k) is performed for 20 to 40 minutes at a temperature of 3° C. to 10° C.

12. The process of claim 1, wherein said centrifuging of step k) is performed for 20 to 50 minutes at a temperature of 30° C. to 40° C.

13. The process of claim 1, wherein, between the fourth and fifth pulses of step f), 20 to 50 $\mu$l of 1M MgCl$_2$, 1 to 4 $\mu$l of 10 mg/ml DNase, and 3 to 7 $\mu$l of 10 mg/ml RNase are added to the suspension.

* * * * *